United States Patent
Money et al.

(10) Patent No.: US 7,346,397 B2
(45) Date of Patent: Mar. 18, 2008

(54) COCHLEAR IMPLANT

(75) Inventors: David Money, Pennant Hills (AU); Tony Nygard, Karlong (AU); Peter Seligman, Essendon (AU); Ibrahim Ibrahim, Lane Cove (AU); Andy L. Zhang, East Melbourne (AU)

(73) Assignee: Cochlear Limited, Lane Cove, NSW (AU)

( * ) Notice: Subject to any disclaimer, the term of this patent is extended or adjusted under 35 U.S.C. 154(b) by 508 days.

(21) Appl. No.: 10/297,870

(22) PCT Filed: Jun. 29, 2001

(86) PCT No.: PCT/AU01/00769

§ 371 (c)(1),
(2), (4) Date: May 9, 2003

(87) PCT Pub. No.: WO02/05590

PCT Pub. Date: Jan. 17, 2002

(65) Prior Publication Data

US 2003/0171787 A1    Sep. 11, 2003

(30) Foreign Application Priority Data

Jun. 30, 2000  (AU) ............... PQ8477
Sep. 19, 2000  (AU) ............... PR0225

(51) Int. Cl.
*A61N 1/36*  (2006.01)
(52) U.S. Cl. .................................. 607/57
(58) Field of Classification Search ........... 607/55–57, 607/136, 137; 623/10
See application file for complete search history.

(56) References Cited

U.S. PATENT DOCUMENTS

| 4,532,930 | A |   | 8/1985 | Crosby et al. |
|-----------|---|---|--------|---------------|
| 5,046,242 | A |   | 9/1991 | Kuzma         |
| 5,279,292 | A | * | 1/1994 | Baumann et al. ........... 607/137 |
| 5,411,467 | A |   | 5/1995 | Hortmann et al. |

(Continued)

FOREIGN PATENT DOCUMENTS

AU    26017/99 A1    3/2000

(Continued)

OTHER PUBLICATIONS

International Search Report dated Jul. 19, 2001; WO02/05590 published Jan. 17, 2002; Inventors: David Money et al.

(Continued)

*Primary Examiner*—George R. Evanisko
(74) *Attorney, Agent, or Firm*—Connolly Bove Lodge & Hutz, LLP (57) ABSTRACT

A totally implantable cochlear implant system forming a single implantable unit (40). The unit (40) has an implantable power source (43) that provides the power requirements of the implantable unit (40). The unit (40) also has an on-board microphone (42) that detects external sounds, such as speech, and outputs acoustic signals representative of the detected sounds. The unit further includes speech processor circuitry (44) that directly receives the acoustic signals from the microphone (42) and converts the signals into stimulation signals representative of the detected sounds. An electrode array (20) suitable for insertion of the cochlea (12) of an implantee receives the stimulation signals and transmits electrical stimulations to the implantee' auditory nerve (9).

43 Claims, 4 Drawing Sheets

U.S. PATENT DOCUMENTS

| | | |
|---|---|---|
| 5,601,617 A | 2/1997 | Loeb et al. |
| 5,645,585 A | 7/1997 | Kuzma |
| 5,814,095 A * | 9/1998 | Muller et al. ................. 607/57 |
| 5,935,166 A | 8/1999 | Kennedy |
| 5,984,953 A | 11/1999 | Sabin et al. |
| 6,067,474 A * | 5/2000 | Schulman et al. ............ 607/57 |
| 6,272,382 B1 * | 8/2001 | Faltys et al. .................. 607/57 |
| 6,308,101 B1 * | 10/2001 | Faltys et al. .................. 607/57 |
| 6,358,281 B1 * | 3/2002 | Berrang et al. ............... 623/10 |
| 6,516,228 B1 * | 2/2003 | Berrang et al. ............... 607/57 |
| 6,531,847 B1 | 3/2003 | Tsukamoto et al. |
| 6,553,263 B1 * | 4/2003 | Meadows et al. ............. 607/61 |
| 6,586,912 B1 | 7/2003 | Tsukamoto et al. |
| 6,636,768 B1 | 10/2003 | Tsukamoto et al. |
| 6,648,914 B2 | 11/2003 | Berrang et al. |
| 6,736,770 B2 | 5/2004 | Leysieffer et al. |
| 6,855,422 B2 | 2/2005 | Magill et al. |
| 6,891,353 B2 | 5/2005 | Tsukamoto et al. |
| 6,894,456 B2 | 5/2005 | Tsukamoto et al. |
| 6,922,591 B2 | 7/2005 | Single |
| 2001/0031909 A1 * | 10/2001 | Faltys et al. |

FOREIGN PATENT DOCUMENTS

| | | |
|---|---|---|
| AU | 26969/99 A | 3/2000 |
| AU | 199926017 B2 | 3/2000 |
| WO | WO-94/17645 A1 | 8/1994 |
| WO | WO-97/44987 A1 | 11/1997 |
| WO | WO 99/06108 | 2/1999 |
| WO | WO 99/41067 | 8/1999 |
| WO | WO-01/39830 A2 | 6/2001 |
| WO | WO 01/74278 A2 | 10/2001 |

OTHER PUBLICATIONS

IPER dated Sep. 27, 2002; (WO 02/05590); Inventors: David Money et al.
Written opinion dated Feb. 18, 2002; WO 02/05590; Inventors: David Money et al.
Written Opinion for PCT/AU01/00769 dated Feb. 18, 2002.

* cited by examiner

COCHLEAR IMPLANT

FIELD OF THE INVENTION

The present invention relates to an implantable device and, in particular, to a fully implantable hearing prosthesis system, such as a cochlear implant.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee. The external component has traditionally consisted of a microphone for detecting sounds, such as speech and environmental sounds, a speech processor that converts speech detected by the microphone into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit has typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound. As such, the implanted stimulator/receiver device has been a relatively passive unit that has relied on the reception of both power and data from the external unit to perform its required function.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee. As such, traditional systems have required a large amount of external componentry and electrical leads to enable the system to function properly.

More recently, due in the main to improvements in technology, the physical dimensions of the speech processor have been able to be reduced, thereby allowing the external componentry to be housed in a small unit capable of being worn behind the ear of the implantee. This unit has allowed the microphone, power unit and the speech processor to be housed in a single unit capable of being discretely worn behind the ear. Despite the development of these so-called behind-the-ear (BTE) units, there still exists the need for an external transmitter coil to be positioned on the side of the implantee's head to allow for the transmission of the coded sound signal from the speech processor and power to the implanted stimulator unit. This need for a transmitter coil further requires leads and additional componentry which have added to the complexity of such systems as well as being quite noticeable. Nevertheless, the introduction of a combined unit capable of being worn behind the ear has greatly improved the visual and aesthetic aspects for cochlear implant implantees.

While traditional cochlear implants have proven very successful in restoring hearing sensation to many people, the construction of the conventional implant with its external electronic components has limited the circumstances in which the implant can be used by an implantee. For example, implantees cannot wear the devices while showering or engaging in water-related activities. Most implantees also do not use the devices whilst asleep due to discomfort caused by the presence of the BTE unit or the external transmitter coil and the likelihood that the alignment between the external transmitter coil and the internal receiver coil will be lost due to movements during sleep. With the increasing desire of cochlear implant implantees to lead a relatively normal life, at least the equivalent of a naturally hearing person, there exists a need to provide a system which allows for total freedom with improved simplicity and reliability, at least at those times when desired by the implantee.

Because of this need, fully implantable systems that do not require external componentry for operation for at least some of their operating life, have been postulated, although none have as yet been commercially available.

An example of one type of system which has been proposed is described in U.S. Pat. No. 6,067,474 by Advanced Bionics Corporation and Alfred E Mann Foundation for Scientific Research. This system attempts to provide all system components implanted in the implantee, and includes a microphone placed in the ear canal which communicates with a conventionally positioned stimulator unit via a conventional RF link. There is further described a battery unit which can be integral with the stimulator unit or separate therefrom. Such a system provides further complications as it requires surgical implantation of a number of components and hence complicates the surgical procedure. The system also maintains the need for a RF link during normal operation between implanted components which increases overall power requirements of the system and unnecessarily drains the internal battery supply. Also, with remotely implanted transmitters required to communicate between internal components, there is also the possibility of increased likelihood of system failure due to component malfunction and as such the procedure required to correct such a device failure becomes further complicated.

Another proposed device is described in International Patent Application No WO 01/39830 to EPIC Biosonics Inc. This system also employs a microphone positioned in the ear canal and an extendible lead connecting the microphone to the implanted stimulator. This proposed system therefore inherits the drawbacks of the system mentioned above as well as introduces a complicated design to the stimulator unit that requires a revised surgical procedure to implant the device.

Generally, the proposed totally implanted cochlear implants suggested to this date, have failed to propose a system which provides the added freedom of a totally implanted device without substantially complicating the surgical procedure and increasing the complexity of the device. Each of the suggested proposals would greatly increase the number of components required to be implanted and in turn would require a further complicated surgical procedure, which may in turn negate the benefits that such a device may provide. Added to this, the increased system complexity and the need to implant connecting leads from the remote components to the implant stimulator, also adds an increased risk of component failure, which again may negate the very benefits that such systems offer.

In the area of hearing aids that deliver mechanical stimulation to the middle ear to amplify the sound detected by the naturally present hair cells in the cochlea, totally implanted devices have also been proposed. International Patent Application No WO 97/44987 to Lesinski and Neukermans, describes a microphone which can be used in such a hearing aid application. The purpose of this particular application is to detect sound and directly apply this sound via mechanical vibrations which can be detected by the perilymph fluid causing a hearing sensation to the intact receptor cells in the cochlea.

The requirements of a hearing aid differ greatly from those of a cochlear implant. In a cochlear implant, the recipient does not possess the functions to detect mechanical vibrations of the perilymph fluid in the cochlear as sound, and as such the stimulation must be delivered in the form of electrical impulses directly to the nerves within the cochlea. In this event, the processing and power requirements of a cochlear implant are significantly different from those of a hearing aid. As the electrode array of a cochlea implant is inserted into the sensitive structures of the cochlea, a cochlea implant is also not readily explantable in the same manner as an implantable hearing aid.

It is also important to recognise that totally implanted hearing aids are designed to operate totally as an implantable device, with the only external componentry used being an external battery charger. Therefore, the implanted microphone is the sole microphone used by the device.

With the above background in mind, there is a need to provide a totally implanted cochlear implant system which does not require external componentry to operate at least for a specific period of time and which provides all components in a single unit able to be implanted by conventional surgical procedures.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is a totally implantable cochlear implant system having an implantable unit comprising:

(i) a hermetically sealed housing including:
  (a) a power source that provides the power requirements of the implantable unit;
  (b) a microphone that detects sounds and outputs acoustic signals representative of said detected sounds; and
  (c) a processor means that directly receives said acoustic signals and converts the signals into stimulation signals representative of the detected sounds; and (ii) an electrode array suitable for insertion in the cochlea of an implantee, the array once inserted being adapted to receive the stimulation signals and output electrical stimulation to the implantee's auditory nerve.

In a preferred embodiment, the hermetically sealed housing is, when used, implanted in a recess formed in the temporal bone adjacent the ear of the implantee that is to receive the implant in a conventional manner as perfected through the implantation of conventional implants.

In a preferred embodiment, the housing is formed from a biocompatible material. Preferably, the housing is manufactured from titanium and is hermetically sealed before implantation into an implantee.

In a preferred embodiment, the unit is formed so as to minimise the need for bone excavation from the temporal bone. The unit preferably has similar dimensions to a conventional implant therefore allowing similar surgical procedures to be employed during implantation.

The housing is preferably made with a smooth surface or surfaces. The housing is also preferably coated with an additional protective layer, such as a layer of silicone or parylene.

In one embodiment, the microphone is housed within the housing. The microphone can be mounted at or adjacent an outer surface of the housing.

The microphone can be a directional dual cavity microphone or a single cavity microphone. The use of a dual-cavity microphone has been determined by the present applicant to provide an effective means of rejecting common mode body-conducted noise emanating from body functions, such as chewing, respiration and blood flow.

It is also envisaged that the microphone can be an electret-type microphone. In another embodiment, the microphone can utilise a piezoelectric polymer, such as polyvinylidene fluoride (PVDF), or a piezoceramic material.

The microphone can comprise a hearing aid microphone as known in the art. An example of a suitable microphone is a Knowles microphone.

Preferably, the microphone will function at a pressure ranging from 1.5 atm to 0.7 atm. This allows a wearer to still use the implant system while recreational diving or during flights on commercial or light aircraft or at elevated locations. The microphone will preferably still operate after being subject to a pressure outside the above range. Preferably, the microphone will survive any exposure to a pressure in the 5 atm to 0.5 atm range.

The electrode array can be any type as is known in the art, such as that described in U.S. Pat. No. 4,532,930. It should be appreciated that the type of array used is not crucial to an understanding of the present invention and any type of array can be used with the system of the present invention provided that it is supported by the system.

The implant system can also include one or more capacitively coupled extracochlea electrodes to support monopolar stimulation as is known in the art.

Electrical connection between the processor means within the housing and the electrode array and the one or more extracochlea electrodes can be provided by respective hermetic and insulated ceramic feedthrouhs. Each feedthrough can be formed using the method described in U.S. Pat. No. 5,046,242, the contents of which are incorporated herein by reference.

The system according to the present invention includes a power source. The power source provides power for the microphone, processor means, electrode array and any other electrical or electronic componentry of the implant system.

The power source can be a battery. The battery is preferably rechargeable. The battery should have a high charge density and be rechargeable over a considerable number of charge/discharge cycles.

The system preferably incorporates a warning system that provides an indication to the implantee that the battery needs recharging. The warning system may generate a unique stimulus signal that results in a sound sensation that the implantee is trained to recognise as an indication that the battery needs recharging. In one embodiment, the sound sensation can comprise a certain tone.

In another embodiment, the implant system incorporates an interrogation means that allows the implantee to determine the charge level of the battery. The interrogation means can be advantageous as it allows an implantee to test the charge level prior to undertaking an activity in which recharging may not be possible or undesirable. For example, an implantee could use the interrogation means to determine the charge level of the power source prior to leaving home. If the charge level is insufficient to last the full day, the implantee may choose to firstly recharge the implanted power source or take a charger with them for when it is required.

The battery can be connected to the componentry within the housing by way of an electrical connector. Such a connector preferably allows for removal of the battery from the system if required. The system is preferably capable of operation while the battery is recharging.

An example of a suitable battery for use with the system of the present invention is a Lithium-Ion cell.

The battery is also preferably electrically insulated from the surrounding housing. The housing preferably incorporates a cradle to receive the battery and provide electrical connection to the battery terminals.

In a preferred embodiment, the system includes a wire antenna coil. The antenna coil is preferably comprised of at least two, and preferably at least three, turns of electrically insulated platinum or gold wire tuned to parallel resonance by a capacitor internal to the housing The electrical insulation of the antenna coil can be provided by a flexible silicone moulding and/or silicone or polyurethane tubing.

The antenna coil is preferably external of the housing. The antenna coil is preferably disposed about a centrally located magnet, the purpose thereof being described below. The magnet can comprise a rare earth permanent magnet hermetically sealed within a titanium case. The magnet within its case is preferably held in the centre of the antenna coil by the silicone moulding, silicone tubing or polyurethane tubing surrounding the antenna coil. In a preferred embodiment, the magnet is removable from the system so as to allow the implantee to undergo magnetic resonance imaging (MRI) scanning.

Electrical connection between the antenna coil and the componentry within the housing can be provided by two hermetic and insulated ceramic feedthroughs or an electrical connector. The ceramic feedthroughs can be formed using the method described in abovementioned U.S. Pat. No. 5,046,242.

The antenna coil can act as part of a radio frequency (RF) link to allow bidirectional data transfer between the system and one or more external devices. The use of appropriate external devices in conjunction with the implanted system allows the system to function, if necessary, as a conventional cochlear implant system. The antenna coil also acts as a power receiver to allow inductive charging of the power source of the implanted system.

The processor means of the invention is preferably mounted on a circuit board within the housing. The circuit board is preferably a flexible board so as to minimise the dimensions of the housing. The processor means preferably comprises a sound processor and a stimulation processor. The sound processor is preferably a speech processor.

It is preferred that the sound processor and stimulation processor be incorporated into a single integrated circuit or microchip in the housing.

The sound processor preferably performs an audio spectral analysis of the acoustic signals and outputs channel amplitude levels. The sound processor can also sort the channel amplitude levels in order of magnitude or flag the spectral maxima as used in the SPEAK strategy developed by Cochlear Ltd.

The stimulation processor preferably performs a stimulation strategy process, stimulus level mapping, and output control. The input to the stimulation processor can come from the internal sound processor or, when utilised, an external sound processor as described below. The role of the stimulation processor is well known in the art and has been performed in all conventional cochlear implant systems to deliver the stimulus to the intracochlea arrays. As such it is considered that a person skilled in the art would understand and appreciate the function performed by the stimulation processor in the current invention.

As described above, the system can preferably be used in association with one or more external devices. The device can, accordingly, operate as a totally implantable device using the implanted microphone to detect sound and implanted processor to process such sound, and also in a manner similar to a conventional cochlear implant system which utilises an external processor unit and external microphone to detect sound and transmit the coded signal for subsequent delivery to the cochlear via the electrodes. The totally implanted cochlear implant of the present invention can therefore offer a choice of operating modes. This is not possible in a totally implantable hearing aid device, as described in the prior art. It does, however, significantly increase the complexity of the cochlear implant system of the present invention in contrast to such hearing aid devices.

In one embodiment, the external device can comprise an external controller for the implanted system. Such a controller can provide a remote means of diagnosing and adjusting system parameters and also provide a means of selecting different speech processing strategies. For example, the controller can allow the implantee or a clinician to diagnose and adjust the sensitivity of the processor means and/or the level of stimulation output by the electrode array.

The external controller also preferably provides the clinician or implantee with a means of interacting with the on-board interrogation means of the system to determine the status of the power source, such as the level of charge of the battery, as well as other useful system information.

The external controller also preferably provides the clinician or implantee with a means of measuring the performance of the processor means and/or the microphone of the implant system.

The external controller can communicate with the implanted unit through inductively coupled and physically aligned internal and external antenna coils providing a transcutaneous radio frequency (RF) link.

In another embodiment, the external device can comprise an external housing containing a sound processor, such as a speech processor. This external housing can also house an external power source, with the external processor adapted to receive acoustic signals from an external microphone. The external microphone can be housed in or on the external housing. In another embodiment, the external microphone can be positioned distal the external housing. Acoustic signals output by the external microphone can be transmitted through a cable or by a wireless means, such as a radio frequency (REF) link. The external microphone can be worn in the ear, including the ear canal, of the implantee or on lapel of the implantee's clothing.

The use of an external device allows the implantee to use the implant in a manner similar to a conventional cochlear implant. This is particularly advantageous as it ensures the implantee can continue to receive sound sensations via the implant even when the implanted system, such as the implanted processor means, has become inactive for any reason.

The use of an external sound processor can also provide the implantee with the option of using sound coding algorithms not supported by the internal sound processor.

The external device can further also be used to recharge the implanted battery. While recharging of the implanted battery is occurring, the external device can preferably act in combination with the implanted system to provide sound sensations to the implantee. In this embodiment, the external unit provides sound coding algorithms to be applied by the implanted stimulator unit, power to the implanted unit and charge to the implanted battery simultaneously.

According to a further aspect, the present invention is an implantable cochlear implant system having an implantable unit adapted to work, when necessary, in conjunction with an external device, wherein:
the implantable unit comprises:
(i) a hermetically sealed housing including:
(a) a power source that provides the power requirements of the implantable unit;
(b) a microphone that detects sounds and outputs acoustic signals representative of said detected sounds; and
(c) a processor means that directly receives said acoustic signals and converts the signals into stimulation signals representative of the detected sounds;
(ii) an electrode array suitable for insertion in the cochlea of an implantee, the array once inserted being adapted to receive the stimulation signals and output electrical stimulation to the implantee's auditory nerve; and
(iii) an antenna coil suitable for implantation in the implantee; and
the external device comprises:
(A) an external power source;
(B) an external microphone that detects sounds and outputs acoustic signals representative of said detected sounds;
(C) an external processor means that receives said acoustic signals of said external microphone and generates a coded signal representative of the detected sounds; and
(D) an external antenna coil adapted to inductively couple with and provide a radio frequency link with the antenna coil of the implantable unit;
wherein the coded signal output by the external processor is transmitted to the electrode array through the radio frequency link.

In this aspect, the processor means of the implantable unit includes a speech processor and a stimulator unit. In one embodiment, the coded signal output by the external processor can, when desired, be transmitted through the radio frequency link to the stimulator unit. The stimulator unit then preferably outputs appropriate stimulation signals to the electrode array in accordance with the coded signal generated by the external processor means.

In one embodiment of this further aspect, the external processor means includes a speech processor.

In a preferred embodiment, the implanted system can detect use by the implantee of the external device. In this regard, the external device can transmit an identification signal to the implanted system. On receipt of the identification signal, the implanted system can, in one embodiment, shutdown its internal microphone and rely solely on reception of the coded signal output by the external processor means and transmitted transcutaneously through the radio frequency link.

In another embodiment, the external device can be used in conjunction with the implantable device to control the operation of the electrode array inserted in the cochlea. This is particularly advantageous when the implanted power source has no charge or when the power source is being recharged as it allows the implantee to still receive hearing sensation despite there being no or insufficient charge in the implanted power source. The capability to operate in conjunction with an external device also provides reassurance to a proposed implantee that they will still be able to receive hearing sensation even if the implanted components of the system, such as the microphone or power source, were to unexpectedly fail.

While the external device can house a charger, a separate battery charger for the implanted battery can also be envisaged. This separate charger can charge the implanted battery through use of the inductive link provided by the respective internal and external antenna coils. A separate charger allows the implanted power source to be recharged when required. The battery charger can be carried by the implantee in a suitable case or harness. In another embodiment, the battery charger can be mounted in a case worn behind the ear of the implantee.

In a still further embodiment, the system can incorporate a deactivation means. Such a deactivation means preferably provides an implantee with a means of quickly and safely deactivating the system when desired.

Operation of the deactivation means can place the system in a shutdown mode whereby electrical stimulation of the cochlea is stopped.

In another embodiment, operation of the deactivation means can lead to complete shutdown of the system.

In yet another embodiment, a first operation of the deactivation means stops electrical stimulation of the cochlea and a second operation of the deactivation means leads to complete shutdown of the system.

The deactivation means preferably incorporates a safety mechanism which prevents inadvertent operation of the deactivation means. The deactivation means can also be used as a means of re-activating the cochlear implant when desired by the implantee.

In one embodiment, the deactivation means can comprise a mechanical switch that is implantable subcutaneously with the system. In such an embodiment, upon the implantee experiencing the desire to shut down the operation of the system, the implantee can physically activate the mechanical switch.

In another embodiment, the deactivation means can be mounted in or on the housing of the system.

In another embodiment, the system can incorporate a resonance circuit, such as a tuned receiver coil, to act as the deactivation means. A circuit in the housing can output a relatively narrow energy spike (voltage or current) that is used to excite the resonance circuit at a regular interval, for example, about every 1 second. The system monitors the amplitude, frequency and/or phase of the waveform following the excitation. When a metal object, such as a magnet or coin, is brought to a position adjacent the implanted tuned coil but external the skin, the response to the excitation changes. This change is noted by the system and generates an "Off" signal. The generation of the "Off" signal may simply stop electrical stimulation of the cochlea or may lead to a shutdown of the system.

The electrical circuitry which outputs the regular narrow energy spike can be electrically separate from the processing circuitry even though it may be physically located in the same integrated circuit or microchip within the housing.

In another embodiment, detection of a certain type of acoustic signal by the implanted microphone triggers shutdown of electrical stimulation or the system. The certain type of acoustic signal can comprise the noise generated by the implantee, or another person, by tapping the skull of the implantee with a finger. For example, detection of a double tap on the skull near the microphone, for example, two taps within a predetermined relatively short period (eg. 0.5 s), could be regarded by the system as an "Off" signal, and so lead to shutdown of electrical stimulation or the system.

The electrical circuitry which processes the detection of the predetermined acoustic signal can be electrically separate from the processing circuitry even though it may be physically located in the same integrated circuit or microchip.

In another embodiment, the implant can utilise another coil wrapped around the existing rare-earth magnet at the centre of the RF receiver coil of the implanted system. Depression of the magnet by the implantee relative to its normal position in the skull induces a current in the coil. This induced current acts as a signal instructing the system to go into a standby mode and so halt electrical stimulation or lead to shutdown of the system.

In a still further embodiment, a portion of the outer surface of the housing can incorporate a switch comprising a compliant membrane positioned above an electrical terminal positioned within the housing. Pressure applied to the compliant membrane transcutaneously by the implantee causes current to flow through the switch. Detection of current flow would move the system into a standby mode and so halt electrical stimulation or lead to shutdown of the system.

In yet a further embodiment, the system can include a piezoelectric membrane implantably positioned so as to be deflectable by the implantee. On deflection, the piezoelectric membrane preferably generates a current of a magnitude sufficient to act as a signal to the system to halt electrical stimulation or lead to shutdown of the system.

The piezoelectric membrane can comprise a piezoceramic or piezoelectric plastics film. The film can comprise one or more films of polyvinylidene fluoride (PVDF) or copolymers incorporating such a polymer.

In another embodiment, the system can include two or more deactivation means. The deactivation means can operate in the same or similar manner or in a different manner. Separate deactivation means can have different functions or simply serve as backups to other deactivation means of the system.

In yet a further embodiment, the implant system can incorporate a telecoil. Telecoils are known in the hearing aid art and are often used in large meeting halls, conference rooms, music halls and the like. Rather than relying on its microphone, the hearing aid is tuned to a broadcast signal that is then amplified by the hearing aid.

In the present invention, the implantee can deactivate the microphone of the system and activate the implanted telecoil. The output of the telecoil is then fed to the implanted processor means for processing in the manner described above. In an alternative embodiment, the telecoil is incorporated into an external device, such as the external housing for the external speech processor, that is useable with the implant.

The provision of a fully implantable system provides an implantee with a hearing sensation while not needing to always rely on external componentry. This allows an implantee to engage in activities, such as water-related activities, while still receiving a hearing sensation from their implant.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
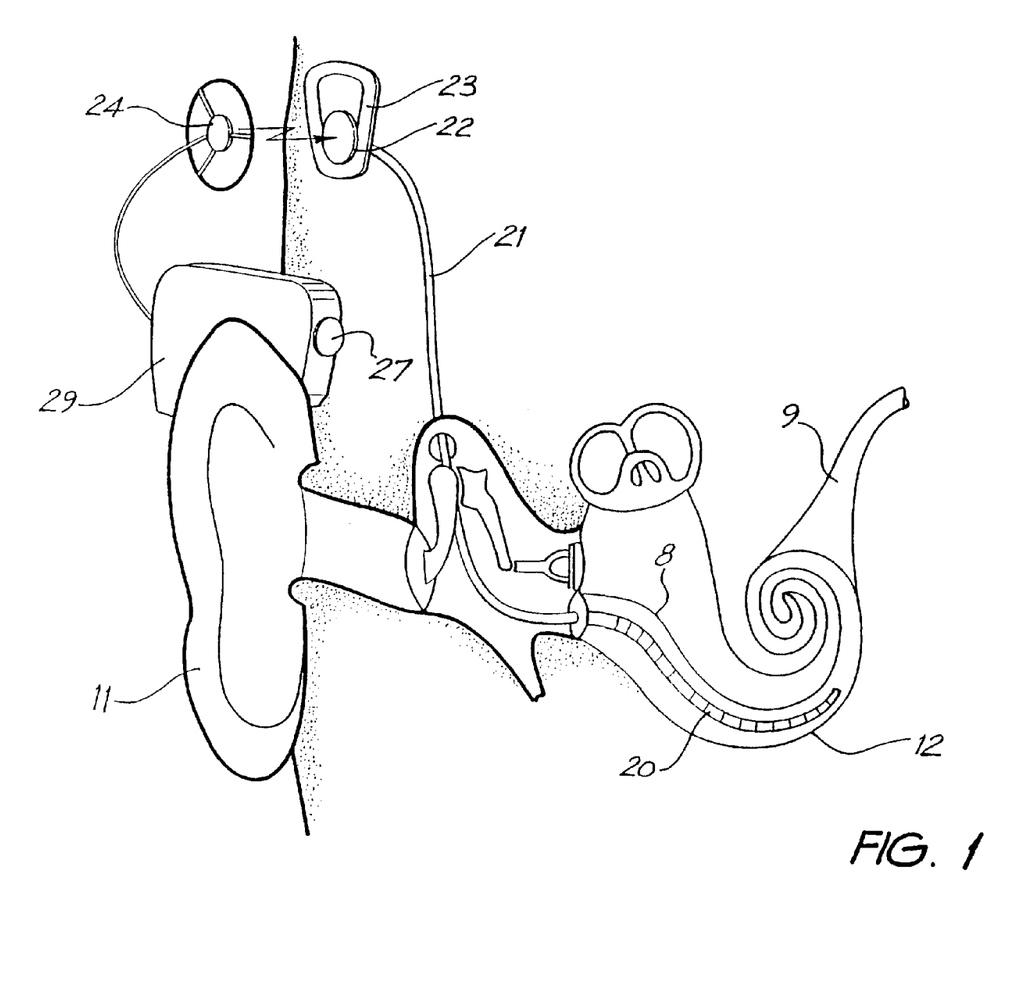
FIG. 1 is a pictorial representation of one example of a prior art cochlear implant system.

Before describing the features of the present invention, it is appropriate to briefly describe the construction of one type of known cochlear implant system with reference to FIG. 1.

Known cochlear implants typically consist of two main components, an external component including an external housing containing a speech processor 29, and an internal component including an implanted receiver and stimulator unit 22. The external component includes a microphone 27. The speech processor 29 is, in this illustration, constructed and arranged so that it can be mounted on and fit behind the outer ear 11. It will be understood that in an alternative version, the housing for the speech processor 29 and/or the microphone 27 may be worn on the body. Attached to the speech processor 29 is an external antenna coil 24 which transmits electrical signals to the implanted unit 22 via a radio frequency (RF) link.

The implanted component includes a receiver antenna coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No. 4,532,930.

In the present invention, the implant is capable of operation, at least for a period of time, without reliance on componentry worn or carried external to the body of the implantee.

Figure 2:
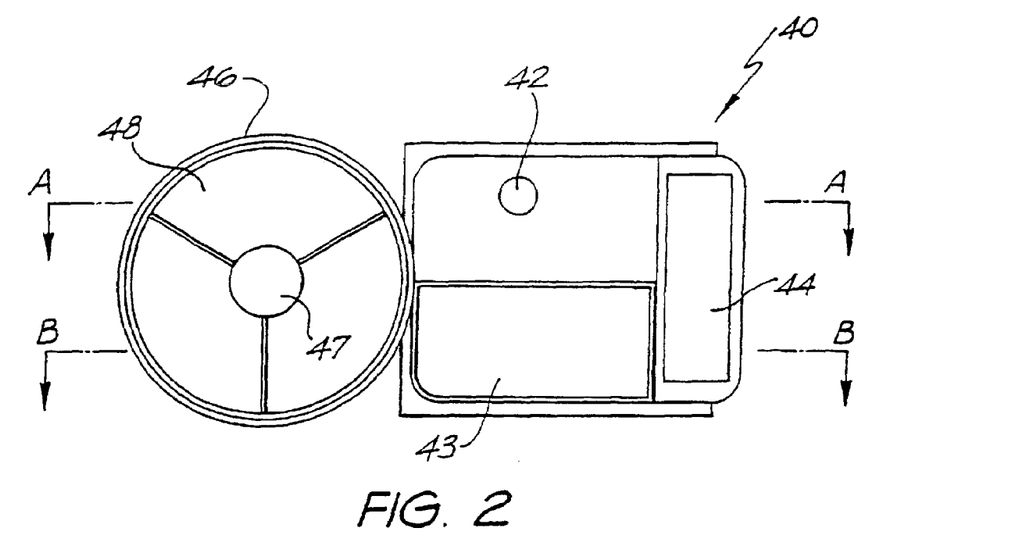
FIG. 2 is a plan view of an implantable housing for an implant according to one embodiment of the present invention.
Figure 2A:
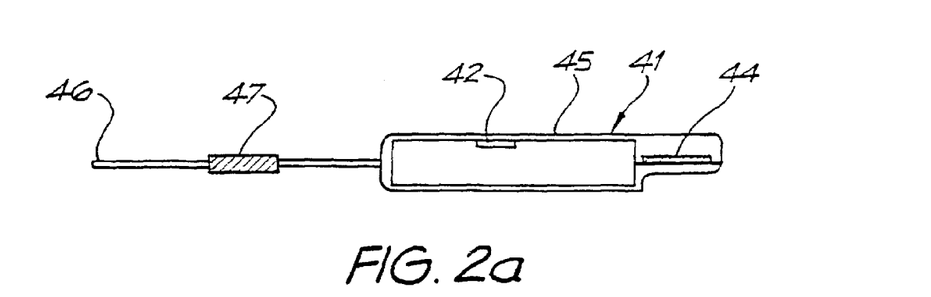
FIG. 2a is a cross-sectional view of the housing of FIG. 2 through line A-A of FIG. 2.
Figure 2B:
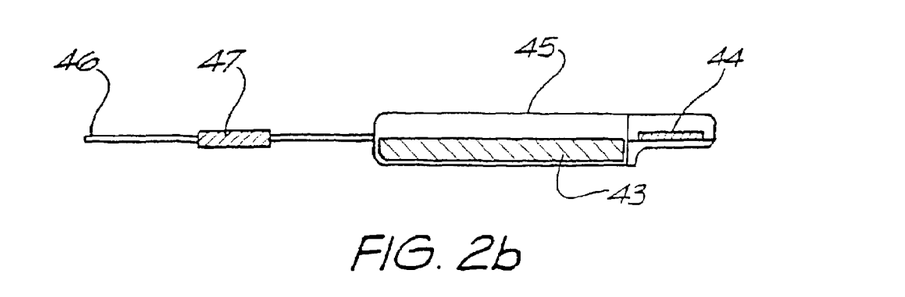
FIG. 2b is a further cross-sectional view of the housing of FIG. 2 through line B-B of FIG. 2.

With reference to FIGS. 2, 2a and 2b, an example of one particular embodiment of the housing of the implant system according to the present invention is shown. The implant 40 is adapted for implantation in a recess formed in the temporal bone adjacent the ear of the implantee that is receiving the implant. The implant 40 has a similar geometry to a conventional implant unit and can be implanted in a manner similar to how the receiver and stimulator unit 22 depicted in FIG. 1 would be implanted. As such, surgical procedures similar to that used for conventional implants are envisaged to be used when implanting the current invention.

The implant 40 comprises a biocompatible and hermetically sealed titanium housing 41 that houses the key electronic circuitry 44 of the implant 40. Also housed within the housing 41 are a microphone 42 and a rechargeable battery 43. Prior to implantation, the housing 41 is coated with a layer of silicone or parylene that serves to further protect the implant. Such a coating is well known in the art and will not be further discussed in this application.

As previously mentioned, the housing 41 is formed so as to minimise the need for bone excavation from the temporal bone at implantation. Whilst the actual dimensions of the housing are not important to the understanding of the invention it should be appreciated that the housing is designed so that the overall dimensions of the implant are substantially the same or only marginally greater than those of a conventional implant. This design allows for similar surgical techniques to be employed during implantation of the current invention as well as with the conventional implant.

In this particular embodiment, the microphone 42 is mounted such that its diaphragm is adjacent one of the surfaces 45 of the housing that faces outwardly following implantation of the housing 41. The depicted microphone 42 is a single cavity microphone but it is envisaged that other microphones, such as a directional dual cavity microphone, could be employed in this system which could perform an equal or similar function.

The electrode array used in conjunction with the implant 40 of the present invention is not shown but can be identical to the array 20 depicted in FIG. 1 or similar. It is, however, preferred that the implant 40 use a Contour™ array in conjunction with corticosteroids to reduce the current required for stimulation.

The rechargeable battery 43 provides power for the microphone 42 and the electronic circuitry 44 housed within the housing 41. Numerous types of batteries could be used with a preferred choice being a Lithium-Ion battery. The type of battery chosen for this application depends greatly on the system requirements, as would be understood by those skilled in the art.

In the depicted embodiment, the battery 43 is non-removable from the housing 41. It will be appreciated that in other embodiments, the housing 41 could be modified to allow removal of the battery 43 by surgically accessing the housing 41.

The implant 40 is capable of operation whilst the battery 43 is being recharged. Further description concerning the recharging process is provided below. In order to isolate the battery from the entire package, a thermal and electrical insulating material is provided between the battery 43 and the surrounding housing 41.

The implant 40 includes an antenna coil 46, which is attached externally of the casing 41. The depicted coil 46 is a 3-turn electrically insulated platinum wire antenna coil. The electrical insulation for the depicted antenna coil 46 is provided by a flexible silicone moulding 48. The antenna coil 46 extends externally from the housing 41 as can be seen in FIG. 2.

The depicted antenna coil 46 is disposed about a centrally located rare earth permanent magnet 47 that is held in the centre of the antenna coil 46 by the silicone moulding 48 surrounding the antenna coil 46. The provision of the magnet 47 assists in the alignment of an external coil unit, such as the external coil 24 depicted in FIG. 1, with the implanted coil 46 via magnetic attractive forces, thereby providing for the system to be used as a conventional cochlear implant system. The magnet 47 is preferably surgically removable so as to allow the implantee to undergo, if required, magnetic resonance imaging (MRI) scanning.

Electrical connection between the coil 46 and the componentry within the housing 41 is provided by two hermetic and insulated ceramic feedthroughs. The coil 46 acts as part of a radio frequency (RF) link to allow bidirectional data transfer between the implant 40 and external devices (described below). The coil 46 also acts a power receiver and so provides a means of inductively charging the battery 43 through the RF link.

The circuitry 44 within the housing is preferably mounted on a flexible circuit board to allow for easier provision of the circuitry within the housing 41. The circuitry 44 includes a speech processor and a stimulation processor incorporated within a single integrated circuit.

With an understanding of the hardware requirements of the current invention, the following description now details how each of the components cooperate together to provide the hearing sensation to the implantee.

Figure 3:
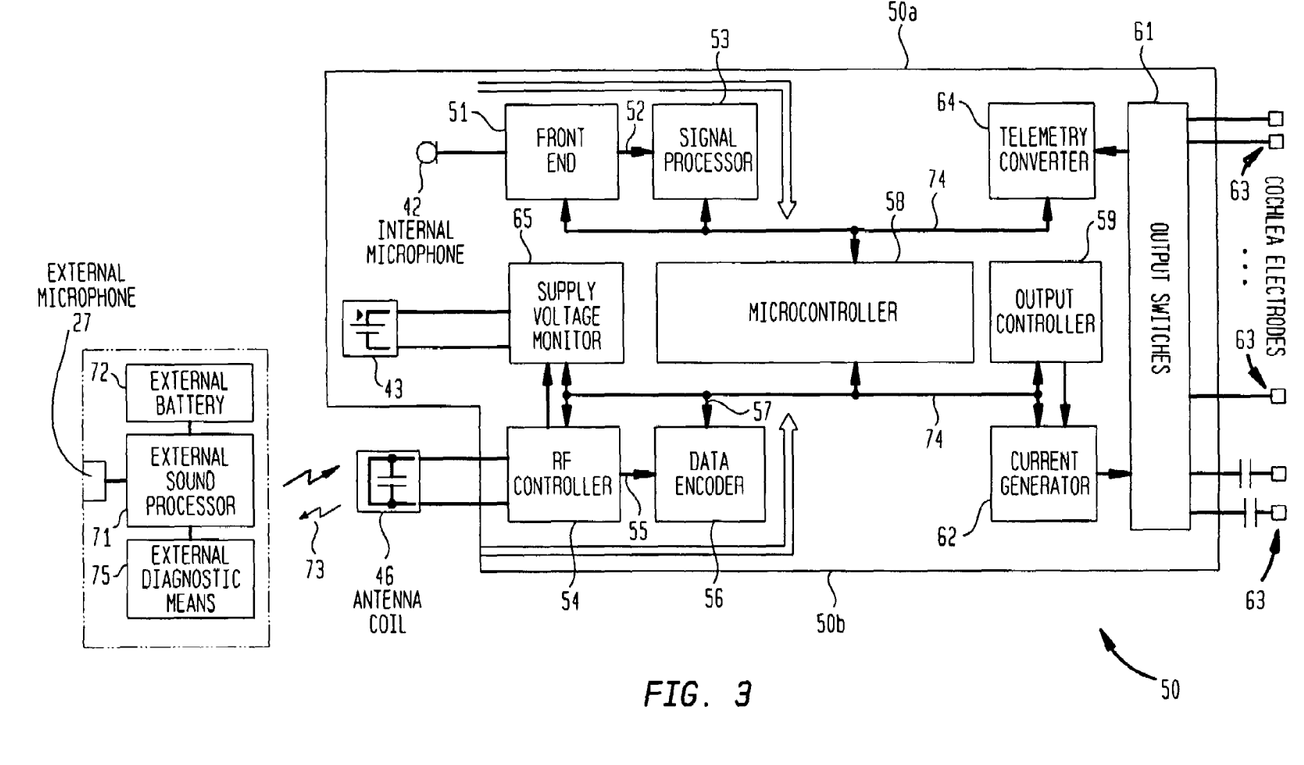
FIG. 3 is a block diagram of one possible electrical architecture of the implant of the present invention.

An overview of the electrical architecture 50 of the circuitry 44 within the housing 41 is provided by FIG. 3. The electrical architecture is based on a microcontroller 58 in the hub to perform the main control function of the implant 40. It should be appreciated that sound processing circuitry and stimulation processor circuitry are well known in the art through their use in conventional cochlear implant systems, and as such the common general principles also apply to the present invention. Such circuitry is specifically designed to meet the system requirements and varies greatly dependant on the type of components used and settings provided for such components.

With that in mind, the current invention essentially has two signal/data paths within the electrical architecture 50 going from left to right as depicted in FIG. 3, namely:

(1) An internal audio signal path 50a consisting of:
—Internal microphone 42—Front end 51—Signal processor 53—Microcontroller 58—Output controller 59—Cochlea electrodes 63; and (2) An external stimulus and control data path 50b consisting of:
—RF Link (antenna coil) 46—RF Controller 54—Data Encoder 56—Microcontroller 58—Output controller 59—Cochlea electrodes 63.

Each of these signal/data paths will now be discussed in turn. The internal audio signal path 50a essentially provides for the operation of the implant as a total unit, whereby the internal microphone 42 detects the external sounds and output sound signals that are then processed by the internal processor and the stimulation is then applied to the auditory nerve via the intracochlea electrodes 63 of an array, such as array 20. Each of the elements of this path will now be discussed in turn.

(a) Internal Microphone 42 and Front End 51

As previously mentioned, the internal microphone 42 is capable of detecting external sounds such as speech from its position within the implanted housing 41. The front end 51, which is also known as an audio pre-processor, essentially includes a preamplifier and an automatic gain control (AGC). The preamplifier amplifies the signal from the internal microphone 42 to a level which can be easily handled by the rest of the signal processing circuit. If the sounds are very soft, a large amount of amplification (gain) is needed and if the sounds are soft, less gain is needed. The amount of gain used is essentially controlled by the AGC. The AGC examines the peaks in the audio signal and adjusts the amplification accordingly to ensure that the sound is within a desired range. In cases where the input sound intensity detected by the internal microphone 42 changes, the AGC follows this change thereby resulting in a signal representative of the original sound at a level sufficient enough to be handled by the signal processing circuit.

(b) Signal Processor 53

In the depicted embodiment, the signal processor 53 runs embedded software and performs an audio spectral analysis of the acoustic signals received from the Front End 51. The signal processor 53 utilises a filter bank to perform this analysis and outputs envelopes of the filtered signals, indicative of the channel amplitude levels. The signal processor 53 also sorts the channel amplitude levels in order of magnitude or flag the spectral maxima as used in the SPEAK strategy developed by Cochlear Ltd.

(c) Microcontroller 58

The microcontroller 58 provides overall supervision, configuration and control of the implant 40 and also performs the function of the stimulation processor. The stimulation processor performs the stimulation strategy process, stimulus level mapping and output control. The input to the stimulation processor comes either from the internal signal processor 53 or an external sound processor (described below). It is possible that the stimulus processor can perform additional stimulation control, not directly derived from the signal processor, such as background conditioning stimulus. The output from the microcontroller 58 provides the direction to stimulate the electrodes 63.

(d) Output Controller 59

The output controller 59 controls the state and timing of the current to the electrodes 63 based on the output from the microcontroller 58. This controller 59 does this by controlling output switches 61 which connect the electrodes 63 to a current generator 62. The output controller 59 also monitors the frequency of "out of compliance" occurrences in the electrodes 63 by recording such occurrences on a counter that can be accessed by a clinician for diagnostic purposes.

(e) Intracochlea Electrodes 63

As previously referred to, the intracochlea electrodes 63 are positioned in the cochlea 12 and provide the stimulation directly to the auditory nerve 9 of the cochlea 12. The circuitry 44 can also control the operation and stimulation output by two or more extracochlea electrodes 63a.

The external stimulus and control data path 50b provides for the operation of the implant 40 together with one or more external devices, such as the external device 29 depicted in FIG. 1. While the implant 40 can operate at least for a limited period as a stand-alone device, the implant 40 can be used in association with such external devices. Any external device uses an external radio frequency (RF) coil, such as coil 94 used for the cochlear implant depicted in FIG. 1, to communicate with the implanted antenna coil 46. In one arrangement, the external device can be used to deactivate and/or activate the implant 40.

As depicted in FIG. 3, one external device that can be used in association with the implant 40 is an external sound processor 71. The external sound processor 71 is powered by an external battery 72 and receives acoustic signals from an external microphone 27. The external microphone 27 can be positioned, in use, on or behind the ear of the implantee or carried at another location by the implantee. The output of the external sound processor 71 is fed, through the RF link 73 provided by the external and internal coils (46,24), to the microcontroller 58, incorporating the stimulation processor, of the implant 40. The external sound processor 71 is normally used in instances where the implanted processor is inactive for any reason, such as a flat battery 43 or due to a malfunction. The external sound processor 71 is also used to provide the implantee with the option of using sound coding algorithms not supported by the internal signal processor 53.

A further external device normally used in association with the implant 40 is a battery charger 72. The charger 72 provides a means of inductively recharging the implanted battery 43 through the RF link 73 when required. The charger 72 can act as a power source for the external device. The battery charger 72 would normally be carried by the implantee in a suitable case or harness.

The external controller also provides the clinician or implantee with a means of interrogating the implant 40 via link 73 to determine the level of charge of the implanted battery 43. The external controller also provides the clinician or implantee with a diagnostic means 75 that measure the performance of the internal signal processor 53 and/or the internal microphone 42 of the implant 40 via link 73.

Each of the elements that make up this path will now be discussed in turn.

(a) RF Receiver (Antenna Coil) 46

The RF Receiver 46 consists of the implanted REF coil as previously described which is able to receive a RF signal transmitted from the external component. The RE link is a bidirectional communications interface. The RF receiver acts as a data receiver, a telemetry pulse transmitter and power receiver during battery charging or when the implant 40 is operating using the power of an external power source 72.

(b) RF Controller 54

The RF controller 54 controls the operation of the RF link 46. The RF controller 54 incorporates RF data comparators which track the RF envelope to optimise data extraction from the link 46. Preferably, both clock and data signals are derived from the RF input provided by the system's RF link 46. If the implant is operated in telemetry mode, a pulse is generated at the RF inputs to cause the LC tuned circuit to ring.

(c) Data Decoder 56

The Data Decoder 56 converts the signals of the RF controller 54 to data output according to the defined embedded protocols. The data output from the data decoder is then sent to the microcontroller 58.

(d) Microcontroller 58

As previously described, the microcontroller 58 provides overall supervision, configuration and control of the implant 40 and also performs the function of the stimulation processor. The stimulation processor performs the stimulation process strategy process, stimulus level mapping and output control. In this instance the input to the stimulation processor comes from the external device via the data decoder 56. The microcontroller 58 then acts on this data and ensures that the required functions are initiated. Programming mode for the microcontroller 58 can be entered via the external RF link by sending a control word in the embedded protocol. The microcontroller 58 communicates with all functional blocks via a microbus 74

In the depicted embodiment, the electrical architecture 50 further incorporates a telemetry converter 64. The telemetry converter 64 measures nerve potential and electrode voltage. It is also used to check the integrity of the memory, diagnostics and test. The output of the telemetry converter 64 is connected to the drivers in the RF controller 54 to allow for transmission of the information to the external diagnostic means 75 via the RF link 73.

The electrical architecture 50 also includes a supply and bias block 65. The supply and bias block 65 performs a number of functions. Firstly, the block 65 provides power on reset to ensure that all circuits of the implant 40 start up in a controlled state at power up. Secondly, the block 65 provides charge management for the battery 43 to ensure that the battery charge cycles are properly maintained. Finally, the block 65 provides supply voltage monitoring to ensure functional operation of and data retention within the circuitry 44.

As described above, the implant 40 can also incorporate an implanted deactivation means. The deactivation means provides the implantee with a means of quickly and safely deactivating the implant 40, without the delay and inconvenience of having to locate, position and activate the external controller. The incorporation of a deactivation means also provides the implantee with the reassurance that they can be away from the external controller and still have the capacity to turn off the implant 40 if the circumstances are such to warrant deactivation.

In one embodiment, on detection of operation of the deactivation means, the microcontroller 58 places the implant 40 in a standby mode where all electrical stimulation to the electrodes 63 of the electrode array, such as array 20, is discontinued. If the implantee again operates the deactivation means, the microcontroller 58 shuts down operation of the implant 40. The implant 40 can then only be re-activated through use of the external controller.

In another embodiment, on detection of operation of the deactivation means, the microcontroller 58 causes the implant 40 to shut down so that no stimulation of the electrodes 63 is possible. If the implantee again operates the deactivation means, the implant may then be re-activated in a safe mode.

The deactivation means can incorporate a safety device which prevents inadvertent operation of the deactivation means.

The deactivation means can be provided by the incorporation of a resonance circuit, such as a tuned receiver coil as part of the implant system. A narrow energy spike (voltage or current) can be output by a waveform generator in the circuitry 44 of the implant 40 and used to excite the resonance circuit at a regular interval, for example about every 1 second. The circuitry 44 can further include a waveform monitoring device that monitors the features of the waveform, such as the amplitude, frequency and/or phase of the waveform following the excitation.

When a metal object, such as a magnet or coin, is brought to a position adjacent the implanted tuned coil but external the skin, the response to the excitation changes. This change is detected by the monitoring means in the circuitry 44 and generates an "Off" signal. The generation of the "Off" signal may simply stop electrical stimulation of the cochlea by the electrodes 63 or may lead to a shutdown of the implant 40.

Other deactivation means are envisaged as being suitable for use with the implant 40 of the present invention.

Detection of a certain type of acoustic signal by the implanted microphone 42 can also be used to trigger shutdown of electrical stimulation of the cochlea 12 by the electrodes 63. The certain type of acoustic signal can comprise the noise generated by the implantee, or another person, by tapping the skull of the implantee with a finger.

The implantee may, in one embodiment, be able to operate the deactivation means by a single tap on the skull. Tests performed by the present applicant suggest that a single relatively gentle tap generates a large impulse response in the microphone 42 of the implant 40. The deactivation means can include a circuit adapted to discriminate such a transient signal from other signals generated by the microphone 42. In one embodiment, the circuit of the deactivation means can detect a signal having a frequency of between about 100 and 200 Hz and an amplitude greater than the other signals generated by the microphone 42 caused by background noise.

Figure 4:
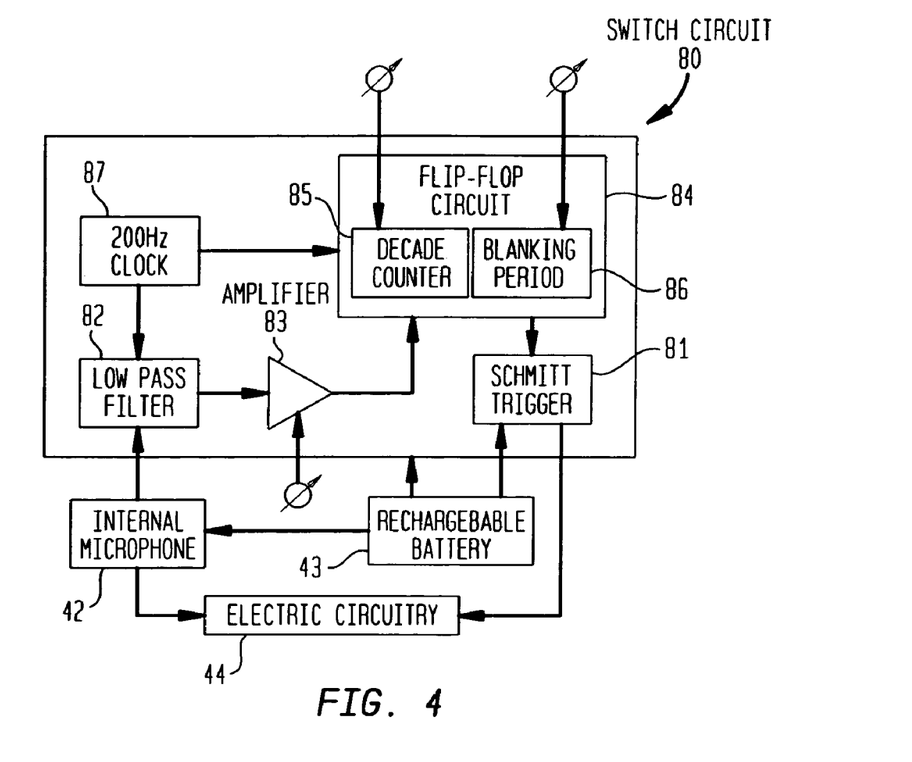
FIG. 4 is a block diagram of a circuit for use with one embodiment of a deactivation means for the cochlear implant.

FIG. 4 is an example of one type of circuit 80 that can be used to detect the generation of deactivation signals output by the microphone 42.

The electrical circuitry 80 which processes the detection of the predetermined acoustic signal is mounted in the same location within the housing 41 as circuitry 44. In the depicted arrangement, the circuitry 80 is electrically separate from the processing circuitry within the microcontroller 58 even though it is physically located in the same integrated circuit as used for the microcontroller 58.

In addition to powering the microphone 42, the implanted battery 43 of the implant 40 powers the circuitry 44 and the switch circuitry 80 through a Schmitt trigger 81, which controls the ON and OFF states of the deactivation means.

The output of the microphone 42 is fed to both the implant circuitry 44 and a low pass filter 82 in the switch circuit 80. The low pass filter 82 filters any high frequency signals output by the microphone 42. It is envisaged that the low pass filter will use switch capacitors.

The output of the low pass filter 82 is amplified by amplifier 83. The gain of the amplifier 83 is adjustable to allow control of the sensitivity of the pickup.

The amplifier 83 produces a high voltage to the input of the flip-flop circuit 84. A 200 Hz clock 87 also provides an appropriate output signal to the low pass filter 82 and the flip-flop circuit 84. The flip-flop circuit 84 has two main functions to control the switching characteristics. Firstly, after responding to a high voltage from the amplifier 83, a decade counter 85 is used to set a sensing duration between about 5 and 50 ms. Secondly, immediately after the sensing period, the circuit is blocked for a blanking period 86 of 640 ms, in which it does not respond to the output of the amplifier 83 regardless of the detection of high or low voltages.

In the depicted circuit 80, the adjustment of the amplifier sensitivity, sensing period and the blanking period is programmed when the implant 40 is fitted to an implantee to suit individual requirements.

The circuit 80 can be modified such that it operates as a switch and so deactivates the implant 40 on detection of a double tap on the skull near the microphone 42. For example, two taps within a predetermined relatively short period (eg. 0.5 s), could be regarded by the system as an "Off" signal and so lead to shutdown of electrical stimulation by the electrodes 63 or the entire system 40.

Figure 5:
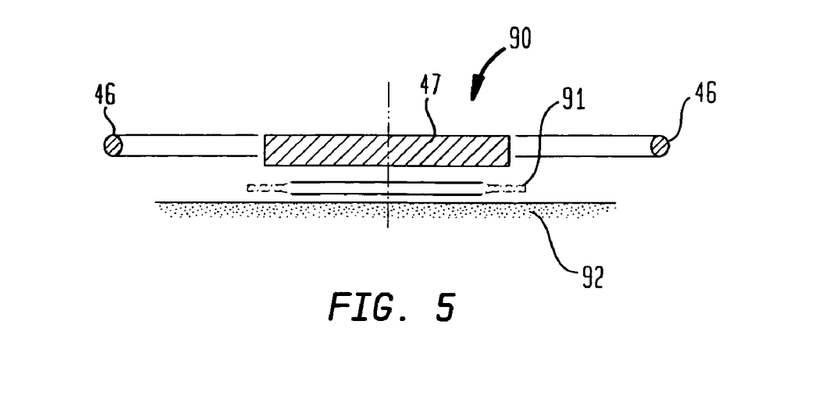
FIG. 5 is a cross-sectional view of another embodiment of a deactivation means for the cochlear implant.

Another embodiment of a deactivation means for the cochlear implant 40 is depicted generally as 90 in FIG. 5. In this embodiment, the implant 40 utilises another coil (i.e. a sensing coil 91) wrapped around the existing rare-earth magnet 47 at the centre of the RF receiver coil 46 as a deactivation means for the implant 40. Depression of the magnet 47 by the implantee relative to its normal position in the bone 92 of the skull induces a current in the sensing coil 91. This induced current can be detected by a current detection circuit in the implant 40 and act as a signal instructing the system 40 to go into a standby mode and so halt electrical stimulation by the electrodes 63 or lead to shutdown of the entire system 40.

In the embodiment depicted in FIG. 5, the magnet 47 is positioned about 1 mm above the surface of the bone 92. The diameter of the magnet 47 is about 10 mm while the diameter of the receiver coil 46 is about 30 mm. Tests performed on the deactivation means 90 suggest that the magnet, when implanted, will be depressed at a speed of about 10 mm/s if tapped by the implantee. Using a samarium cobalt magnet 47 having a flux density at so magnet surface of 0.17T, the output voltage of the sensing coil 91 is estimated to be about 30 μV per turn. The generation of this voltage can be detected by a circuit, such as circuit 80 with suitable modifications, and used to deactivate the implant 40 when required.

A portion of the outer surface of the housing 41 can incorporate a switch comprising a compliant membrane positioned above an electrical terminal positioned within the housing 41. Pressure applied to the compliant membrane transcutaneously by the implantee causes current to flow through the switch. Detection of current flow would move the implant 40 into a standby mode and so halt electrical stimulation or lead to shutdown of the implant 40.

The implant 40 can instead include a piezoelectric membrane which is deflectable by the implantee. On deflection, the piezoelectric membrane would preferably generate a current of a magnitude sufficient to act as a signal to the microcontroller 58 to halt electrical stimulation by the electrodes 63 or lead to shutdown of the implant 40.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An implantable unit of a cochlear implant system comprising:
   a hermetically sealed housing having disposed therein a power source configured to provide power to said implantable unit; a microphone configured to detect sounds and to output acoustic signals representative of said detected sounds; and a processor configured to convert said acoustic signals into at least one stimulation signal representative of said detected sounds;
   an electrode array configured to provide electrical stimulation to an implantee's auditory nerve based on said stimulation signals; and
   a deactivation system configured to monitor acoustic signals output by said microphone and to trigger shutdown of said electrical stimulation in response to detection of a predetermined acoustic signal.

2. The implantable unit of claim 1 wherein said predetermined acoustic signal is a noise generated by tapping the implantee's head.

3. The implantable unit of claim 2 wherein said predetermined acoustic signal is a noise generated by tapping the implantee's head twice within a predetermined period of time.

4. The implantable unit of claim 1 wherein said microphone is housed within said housing.

5. The implantable unit of claim 1 wherein said microphone is positioned adjacent to a surface of said housing such that said microphone faces outwardly upon implantation of said housing in the implantee.

6. The implantable unit of claim 5 wherein said microphone is configured to function within a pressure ranging from about 0.7 atm to about 1.5 atm.

7. The implantable unit of claim 1 wherein said power source is configured to provide power for said microphone, said processor, said electrode array and any other electrical or electronic componentry of said cochlear implant system.

8. The implantable unit of claim 7 wherein said system further comprises a warning system configured to provide an indication to the implantee when said power source contains a charge level that is below a predetermined level.

9. The implantable unit of claim 8 wherein said warning system is configured to generate a stimulus signal that the implantee is trained to recognize that said power source contains a charge level that is below a predetermined level.

10. The implantable unit of claim 8 wherein said warning system further comprises an interrogation system configured to provide information in response to a query by the implantee to determine a charge level of said power source.

11. The implantable unit of claim 1 further comprising a wire antenna receiver coil external of said housing that is configured to act as part of a radio frequency (RF) link to allow bidirectional data transfer between said implantable unit and one or more external devices.

12. The implantable unit of claim 11 further comprising a magnet wherein said wire antenna receiver coil is disposed about said magnet.

13. The implantable unit of claim 11 wherein said wire antenna receiver coil is further configured to receive power for inductively charging said power source.

14. The implantable unit of claim 11 wherein said processor comprises a speech processor and a stimulation processor.

15. The implantable unit of claim 1 wherein said processor is mounted on a circuit board within said housing.

16. The implantable unit of claim 1 wherein said totally implantable cochlear implant system further comprises a telecoil.

17. The implantable unit of claim 1 wherein said deactivation system is mounted in or on said housing.

18. A cochlear implant system having an implantable unit configured to function with an external device, wherein:
said implantable unit comprises:
a hermetically sealed housing comprising:
a power source that provides the power requirements of the implantable unit:
a microphone that detects sounds and outputs acoustic signals representative of said detected sounds; and
a processor configured to directly receive said acoustic signals and to convert said acoustic signals into at least one stimulation signal representative of the detected sounds;
an electrode array suitable for insertion in the cochlea of an implantee, the array once inserted being adapted to provide electrical stimulation to the implantee's auditory nerve based on said stimulation signals; and
an antenna coil suitable for implantation in the implantee; and
a deactivation system configured to monitor acoustic signals output by said microphone and to trigger shutdown of electrical stimulation of the implantee's auditory nerve on detection of a predetermined type of acoustic signal; and
wherein said external device comprises:
an external power source;
an external microphone that detects sounds and outputs acoustic signals representative of said detected sounds;
an external processor configured to receive said acoustic signals of said external microphone and to generate a coded signal representative of the detected sounds; and
an external antenna coil adapted to inductively couple with said antenna coil of the implantable unit and to provide a radio frequency link between said implantable unit and said external device;
wherein said coded signal output by said external processor is transmitted to said electrode array through said radio frequency link.

19. The implantable unit of claim 18 wherein said microphone is positioned adjacent to a surface of said housing such that said microphone faces outwardly upon implantation of said housing in the implantee.

20. The implantable unit of claim 19 wherein said microphone is configured to function within a pressure ranging from about 0.7 atm to about 1.5 atm.

21. The implantable unit of claim 18 wherein said power source is configured to provide power for said microphone, said processor, said electrode array and any other electrical or electronic componentry of said cochlear implant system.

22. The implantable unit of claim 21 wherein said system further comprises a warning system configured to provide an indication to the implantee when said power source contains a charge level that is below a predetermined level.

23. The implantable unit of claim 22 wherein said warning system is configured to generate a stimulus signal that the implantee is trained to recognize that said power source contains a charge level that is below a predetermined level.

24. The implantable unit of claim 22 wherein said warning system further comprises an interrogation system configured to provide information in response to a query by the implantee to determine a charge level of said power source.

25. The implantable unit of claim 18 further comprising a wire antenna receiver coil external of said housing that is configured to act as part of a radio frequency (RE) link to allow bidirectional data transfer between said implantable unit and one or more external devices.

26. The implantable unit of claim 25 further comprising a magnet wherein said wire antenna receiver coil is disposed about said magnet.

27. The implantable unit of claim 25 wherein said wire antenna receiver coil is further configured to receive power for inductively charging said power source.

28. The implantable unit of claim 25 wherein said processor comprises a speech processor and a stimulation processor.

29. The implantable unit of claim 18 wherein said processor is mounted on a circuit board within said housing.

30. The implantable unit of claim 18 wherein said totally implantable cochlear implant system further comprises a telecoil.

31. The implantable unit of claim 18 wherein said deactivation system is mounted in or on said housing.

32. The implantable unit of claim 18 wherein said predetermined acoustic signal is a noise generated by tapping the implantee's.

33. The implantable unit of claim 32 wherein said predetermined acoustic signal is a noise generated by tapping the implantee's head twice within a predetermined period of time.

34. A totally implantable cochlear implant system having an implantable unit comprising:
a hermetically sealed housing comprising:
a power source that provides the power requirements of the implantable unit;
a microphone that detects sounds and outputs acoustic signals representative of said detected sounds; and
a processor configured to directly receive said acoustic signals and to convert said acoustic signals into at least one stimulation signal representative of the detected sounds;
an electrode array suitable for insertion in the cochlea of an implantee, the array once inserted being adapted to provide electrical stimulation to the implantee's auditory nerve based on said stimulation signals; and
a deactivation system, wherein a first operation of said deactivation system stops electrical stimulation of the cochlea by said electrode array and a subsequent operation of said deactivation system results in complete shutdown of said totally implantable cochlear implant system.

35. The system of claim 34 wherein a first operation of said deactivation system places said totally implantable cochlear implant system in a shutdown mode whereby electrical stimulation of the cochlea by said electrode array is stopped.

36. The system of claim 34 wherein a first operation of said deactivation system results in complete shutdown of said totally implantable cochlear implant system.

37. The system of claim 34 wherein said deactivation system comprises a mechanical switch that is implantable subcutaneously with said totally implantable cochlear implant system.

38. The system of claim 34 wherein said deactivation system is mounted in or on the housing of said totally implantable cochlear implant system.

39. The system of claim 34 wherein said deactivation system is configured to generate a waveform, to monitor said generated waveform, to generate a deactivation signal in response to detecting a predefined change in said waveform and to stop said electrical stimulation of the implantee's cochlea.

40. The implantable unit of claim 39 wherein said deactivation system comprises a resonance circuit; a waveform generator circuit configured to generate an energy waveform that excites the resonance circuit at a regular interval; and a waveform monitoring device configured to monitor one or more features of said generated waveform following the excitation, to detect a predefined change in at least one property of said waveform resulting from a metal object being brought to a position adjacent to said resonance circuit but external the skin of the implantee, and to generate a deactivation signal in response to detecting said predefined change in said waveform to halt said electrical stimulation.

41. The system of claim 34 wherein said deactivation system is configured to monitor acoustic signals output by said microphone and to trigger shutdown of electrical stimulation of the cochlea by said electrode array on detection of a predetermined type of acoustic signal.

42. The implantable unit of claim 41 wherein said predetermined acoustic signal is a noise generated by tapping the implantee's head.

43. The implantable unit of claim 42 wherein said predetermined acoustic signal is a noise generated by tapping the implantee's head twice within a predetermined period of time.

* * * * *

UNITED STATES PATENT AND TRADEMARK OFFICE
CERTIFICATE OF CORRECTION

| | |
|---|---|
| PATENT NO. | : 7,346,397 B2 |
| APPLICATION NO. | : 10/297870 |
| DATED | : March 18, 2008 |
| INVENTOR(S) | : David K. Money et al. |

It is certified that error appears in the above-identified patent and that said Letters Patent is hereby corrected as shown below:

On the Title Page:
Item (75)

In the Inventors Section, the city of residence of Tony Nygard is listed as "Karlong" and should be listed as --Kariong--.

On the Title Page Item (57)
In the Abstract, line 13 reads "electrical stimulations to the ~~implantee'auditory~~ nerve (9)." and should be amended to
--electrical stimulations to the implantee's auditory nerve (9).--

In column 5, line 67 reads "by a capacitor internal to the housing The electrical insulation" and should be amended to --by a capacitor internal to the housing.

The electrical insulation--.

(*Please Note: A period should follow the word "housing" and the following word "The" should begin a new paragraph.*)

In column 14, line 26 reads "coil 94 used for the cochlear implant depicted in FIG. 1, to" and should be amended to --coil 24 used for the cochlear implant depicted in FIG. 1, to--.

In column 14, line 63 reads "The RF Receiver 46 consists of the implanted REF coil as" and should be amended to --The RF Receiver 46 consists of the implanted RF coil as--.

In column 14, line 65 reads "transmitted from the external component. The RE link is a" should be amended to --transmitted from the external component. The RF link is a--.

In column 17, line 48 reads "colbalt magnet 47 having a flux density at so magnet surface" should be amended to --colbalt magnet 47 having a flux density at magnet surface--.

UNITED STATES PATENT AND TRADEMARK OFFICE
CERTIFICATE OF CORRECTION

PATENT NO. : 7,346,397 B2
APPLICATION NO. : 10/297870
DATED : March 18, 2008
INVENTOR(S) : David K. Money et al.

It is certified that error appears in the above-identified patent and that said Letters Patent is hereby corrected as shown below:

In claim 6, column 18, line 39 is listed as "from about 0.7 atm to about 1.5 atm." and should be amended to --from about 0.7 atm to about 1.5 atm.--

In claim 25, column 20, line 7 is listed as "configured to act as part of a radio frequency (RE) link to" and should be amended to --configured to act as part of a radio frequency (RF) link to--.

Signed and Sealed this

Eighth Day of July, 2008

JON W. DUDAS
*Director of the United States Patent and Trademark Office*